(12) United States Patent
Kopf-Sill

(10) Patent No.: US 6,420,143 B1
(45) Date of Patent: Jul. 16, 2002

(54) METHODS AND SYSTEMS FOR PERFORMING SUPERHEATED REACTIONS IN MICROSCALE FLUIDIC SYSTEMS

(75) Inventor: Anne R. Kopf-Sill, Portola Valley, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/023,693

(22) Filed: Feb. 13, 1998

(51) Int. Cl.[7] .................... C12P 19/34; B32B 5/02; C07K 17/00; C07H 21/00
(52) U.S. Cl. .................. 435/91.1; 435/91.2; 422/131; 422/138; 530/333; 536/25.3
(58) Field of Search ............... 435/91.1, 91.2; 536/25.3; 530/333; 422/131, 138

(56) References Cited

U.S. PATENT DOCUMENTS

| | | | |
|---|---|---|---|
| 4,252,118 A | * | 2/1981 | Richard et al. .......... 128/218 P |
| 4,390,403 A | | 6/1983 | Batchelder |
| 4,683,195 A | | 7/1987 | Mullis et al. |
| 4,683,202 A | | 7/1987 | Mullis |
| 4,800,159 A | | 1/1989 | Mullis et al. |
| 4,889,818 A | | 12/1989 | Gelfand et al. |
| 4,908,112 A | | 3/1990 | Pace |
| 4,965,188 A | | 10/1990 | Mullis et al. |
| 5,126,022 A | | 6/1992 | Soane et al. |
| 5,333,675 A | | 8/1994 | Mullis et al. |
| 5,415,839 A | * | 5/1995 | Zaun et al. .................. 422/64 |
| 5,498,392 A | | 3/1996 | Wilding et al. |
| 5,571,410 A | | 11/1996 | Swedberg et al. |
| 5,585,069 A | | 12/1996 | Zanzucchi et al. |
| 5,593,838 A | | 1/1997 | Zanzucchi et al. |
| 5,603,351 A | | 2/1997 | Cherukuri et al. |
| 5,635,538 A | | 6/1997 | Wilding et al. |
| 5,637,469 A | | 6/1997 | Wilding et al. |
| 5,840,276 A | * | 11/1998 | Apfel ................... 424/9.52 |
| 5,965,410 A | * | 10/1999 | Chow et al. ............... 435/91.2 |

FOREIGN PATENT DOCUMENTS

| | | | |
|---|---|---|---|
| WO | WO 96/04547 | 2/1996 | ......... G01N/27/00 |
| WO | WO 97/02357 | 1/1997 | ......... C12P/19/34 |

OTHER PUBLICATIONS

Dasgupta, P.K. et al., "Electroosmosis: A Reliable fluid Propulsion System for Flow Injection Analysis," *Anal. Chem.*, 66:1792–1798 (1994).
Jacobson, S.C. et al., "Fused Quartz Substrates for Microchip Electrophoresis," *Anal. Chem.*, 67:2059–2063 (1995).
Manz, A. et al., "Electroosmotic pumgin and electrophoretic separations for miniaturized chemical analysis systems," *J. Micromech. Microeng.* 4:257–265 (1994).
Ramsey, J.M. et al., "Microfabricated chemical measurement systems," *Nature Med.* 1:1093–1096 (1995).
Seiler, K. et al., "Planar Glass Chips for Capillary Electrophoresis: Repetitive Sample Injection, Quantitation, and Separation Efficiency," *Anal. Chem.* 65:1481–1488 (1993).
Seiler, K. et al., "Electroosmotic Pumping and Valveless Control of Fluid Flow within a Manifold of Capillaries on a Glass Chip," *Anal. Chem.* 66:3485–3491 (1994).

* cited by examiner

*Primary Examiner*—Ardin H. Marschel
(74) *Attorney, Agent, or Firm*—Matthew B. Murphy; Gulshan H. Shaver

(57) ABSTRACT

The present invention is generally directed to methods and systems for performing chemical and biochemical reactions at superheated temperatures by carrying out the reactions in microscale fluidic channels. Also provided are applications of these methods and systems, as well as ancillary systems for use with these methods and systems in monitoring and controlling the performance of the methods of the invention.

45 Claims, 3 Drawing Sheets

METHODS AND SYSTEMS FOR PERFORMING SUPERHEATED REACTIONS IN MICROSCALE FLUIDIC SYSTEMS

BACKGROUND OF THE INVENTION

Microfluidic analytical systems have been gaining substantial interest for use in performing myriad chemical and biochemical analyses and syntheses. For example, such systems have been described for use in performing nucleic acid amplification reactions (See U.S. Pat. Nos. 5,498,392 and 5,587,128), for use in performing high throughput screening assays, e.g., in drug discovery operations (See commonly owned Published International Application No. WO 98/00231), for use in nucleic acid separations (See Published PCT Application No. WO 96/04547), and for a variety of other uses. These microfluidic systems generally combine the advantages of low volume/high throughput assay systems, with the reproducibility and ease of use of highly automated systems.

Because of the above advantages, it would generally be desirable to expand the applications for which these systems are used, as well as expand the scope of the advantages which such systems offer over conventional assay systems, e.g., faster throughput, lower volumes, etc. One area of particular interest is the performance of temperature responsive reactions, e.g., reactions that progress faster at higher temperatures, or require a substantially elevated base temperature to occur. In many cases, desirable chemical and biochemical reactions can be substantially expedited by performing the reaction at substantially elevated temperatures. However, in fluid systems, and especially aqueous fluid systems, a practical limit on the temperature of the operation generally is imposed by the boiling point of the fluid. For example, in aqueous systems, the boiling temperature of the fluid at or near 100° C. is the effective maximum achievable temperature at ambient pressures of approximately 1 atm.

In order to perform reactions that utilize or even require temperatures that are above the boiling point for the fluid reactants, the use of pressure sealed reaction vessels are typically required to elevate the boiling temperature of the fluid by increasing the ambient pressure for the reaction. Unfortunately, in many reaction systems, the use of such sealed containers is impracticable. For example, in microfluidic systems, the extremely small scale of the fluid carrying elements of the system and thus the fluid volumes used, as well as the nature of the fluid transport systems employed, typically prohibit the use of pressure sealed reaction containers.

Additional concerns are raised in microfluidic systems where the presence of a bubble or bubbles, e.g., from inadvertent boiling of fluids within the system, can have extremely detrimental effects on the system by significantly fouling or plugging channels of the system. Such fouling can inhibit or completely block the ability to move fluids through the channels of the system, as well as the ability to monitor the contents of the system, e.g., using amperometric or potentiometric means. Further, in microfluidic devices employing electrokinetic material transport systems to move materials through the microscale channels of the device, such fouling can result in a cascade effect where the blockage results in higher current densities through the remaining portions of the channel which leads to greater heating. This greater heating, in turn, leads to more bubbles within the channels from boiling of the fluids.

It would therefore be desirable to be able to perform reactions at temperature levels that are at or substantially above the boiling point of the fluids used in the reaction, while benefiting from the advantages of microfluidic systems. The present invention meets these and a variety of other needs.

SUMMARY OF THE INVENTION

The present invention is generally directed to methods and systems for performing chemical and biochemical reactions at superheated temperatures by carrying out the reactions in microscale fluidic channels. Also provided are applications of these methods and systems, as well as ancillary systems for use with these methods and systems in monitoring and controlling the performance of the methods of the invention.

In one aspect, the present invention provides methods for performing reactions at superheated temperatures, which comprise placing at least a first reactant in a microscale fluidic channel. An effective level of energy then is applied to the fluid in the microscale channel, whereby the fluid is heated to a superheated temperature without boiling the fluid within the channel.

In a related aspect, the invention also provides a method for performing a reaction at a superheated temperature, which comprises providing a substrate having at least a first microscale channel disposed therein. The substrate is in communication with an energy source that delivers the sufficient level of energy to the contents of the microscale channel to heat said contents to superheated temperatures. The first reactant then is placed into the microscale channel, and the sufficient level of energy from said energy source is applied to the microscale channel to heat the contents of the channel to superheated temperatures.

In a further aspect, the present invention also provides systems for carrying out the methods described herein. In particular, these systems comprise a microfluidic device that includes at least a first substrate having a microscale channel disposed therein, where the microscale channel has at least first and second unintersected termini. A heating system is also included to apply energy to the microscale channel to heat a fluid in the channel to superheated temperatures, without boiling the fluid in the channel. Further, a controller is also provided for maintaining the energy applied from the heating system to the microscale channel at a level sufficient to superheat contents of the microscale channel without boiling the contents of the channel.

DETAILED DESCRIPTION OF THE INVENTION

Figure 1:
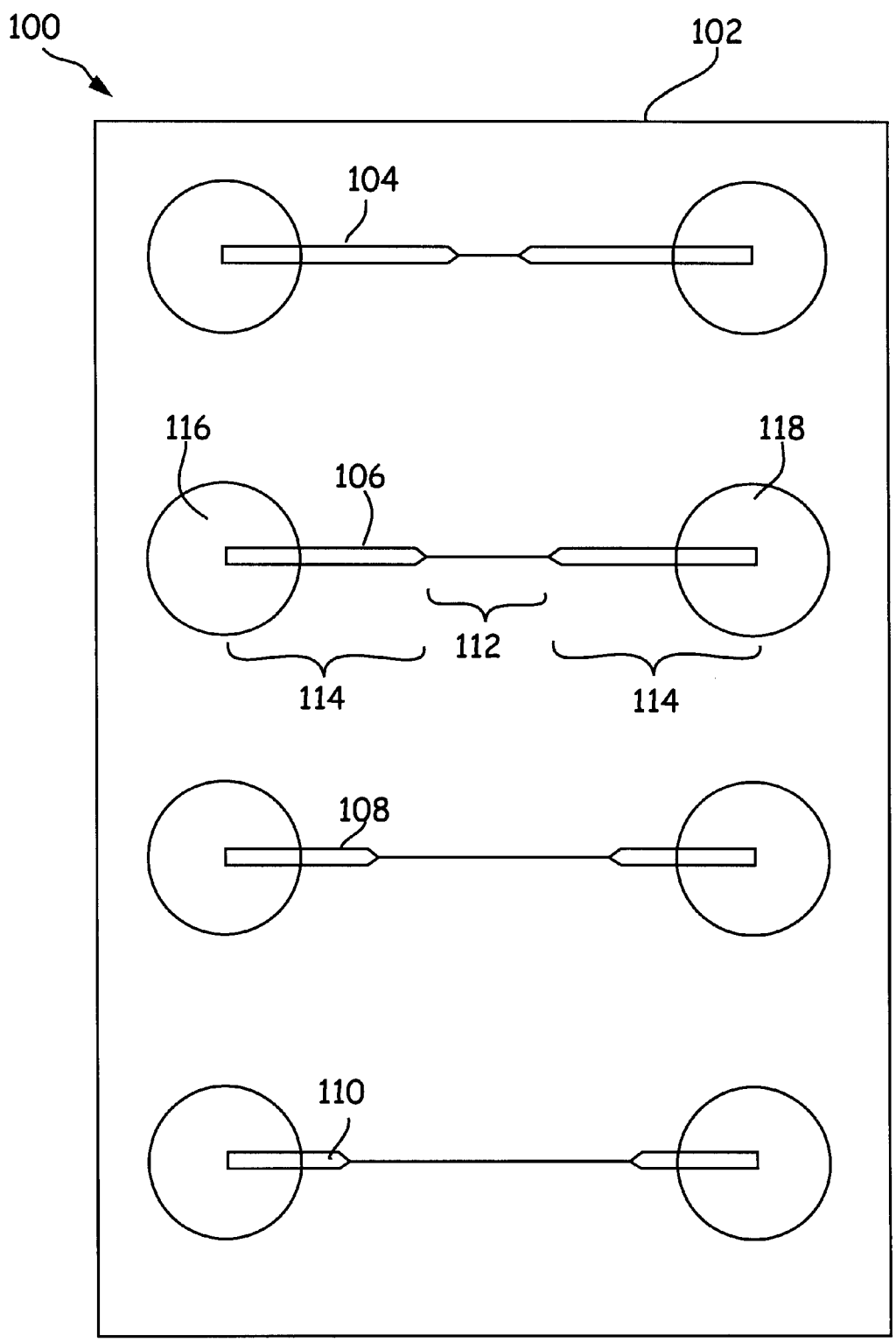
FIG. 1 illustrates an expanded view of a microfluidic device and channel structure for performing superheated reactions according to the present invention.

The present invention generally provides methods and systems for performing chemical, biological or biochemical reactions in fluid systems. More particularly, the methods and systems of the invention permit the performance of such reactions at superheated temperatures, i.e., above the boiling temperature for the fluid at the ambient pressure of the system. Such methods and systems are generally useful in speeding reactions that are temperature dependant, as well as for carrying out reactions that require temperatures in excess of the boiling temperatures for the fluids used. Examples of such reactions include reactions that require a thermal denaturation step such as enzyme inactivation reactions, nucleic acid amplification reactions, and the like.

Typically, the methods and systems of the invention operate by placing the fluid reactant or reactants into a microscale fluidic channel, and heating the fluid within the channel to superheated temperatures. Included among the benefits of the present invention is the fact that the systems and methods described herein allow fluid contained within one or more microscale channels to be heated to superheated temperatures without boiling the fluid that is contained within those channels. In addition to the benefits normally available in performing superheated reactions, e.g., higher reaction temperatures in aqueous systems, the present invention is also particularly useful in microscale systems where the generation of a bubble within a channel can have fatal consequences for the system, e.g., blocking material transport, current flow, etc. through that channel.

Without being bound to a particular theory of operation, it is believed that the microscale channels fabricated by traditional microfabrication methods, e.g., photolithography, chemical vapor deposition, wet chemical etching, injection molding, etc., have surfaces that are resistant to bubble nucleation during the boiling process. As such, fluids within channels having such surfaces will not boil at their expected boiling points.

As used herein and as noted above, the term "superheated temperature" for a given fluid or mixture of fluids, refers to a temperature that is greater than the temperature at which the particular fluid or fluids will boil at the ambient pressure for the system. In preferred aspects, the present invention provides heating of fluids to temperatures more than 5° C. above the boiling point of the fluids, more preferably, greater than 10° C., 20° C., 30°, 40° C. and even 50° C. over the boiling point of the fluids. For example, in the case of a pure water system, superheated temperatures are generally greater than 100° C. at 1 atm pressure. In many instances therefore, the methods and systems of the present invention provide heating of fluids, and particularly aqueous fluids, within microscale channels to temperatures well in excess of 100° C., 105° C., 110° C., 120° C., 130° C., often in excess of 140° C., and in some cases in excess of 150° C., without boiling the aqueous fluid that is contained within the heated channel. Of course, variations in ambient pressure also bring corresponding changes in the boiling temperature of fluids at that pressure. As used herein, the term "aqueous system" generally refers to a fluid composition that is made up substantially of water, e.g., greater than 30% (v/v), typically greater than 50%, often greater than 80%, preferably greater than 90% and more preferably greater than 95% water (v/v). Although described in terms of aqueous systems, it will be appreciated that the present invention is equally applicable to non-aqueous systems, e.g., organic solutions, etc.

As described above, the methods and systems of the present invention operate through the placement of the fluid reactants into a microscale channel that is typically incorporated into the body of a microfluidic device. As used herein, the term microscale or microfluidic refers to a structural element, and typically a fluidic element, e.g., a channel or chamber, which has at least one cross-sectional dimension, e.g., depth width or both, that is between about 0.1 μm and about 500 μm, preferably between about 1 μm and about 200 μm, and in many cases, between about 10 μm and about 100 μm.

The body structures including the microscale channel or channels, as described herein, can be fabricated from a variety of different substrate materials. For example, in many instances, the body structure and channel or channel networks are microfabricated. As such, substrate materials are often selected based upon their compatibility with known microfabrication techniques, e.g., photolithography, wet chemical etching, laser ablation, air abrasion techniques, injection molding, embossing, LIGA, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like.

In the case of semiconductive materials, it will often be desirable to provide an insulating coating or layer, e.g., silicon oxide, over the substrate material, and particularly in those applications where electric fields are to be applied to the device or its contents.

In alternate preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping using metal electroforms, e.g., LIGA methods, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, and which is incorporated herein by reference in its entirety for all purposes.

Substrates can also come in a variety of shapes and forms, including planar forms, e.g., in a chip format, or tubular forms, e.g., a capillary format. The specific shape will typically vary depending upon the particular application for which the system is utilized. For example, systems employing complex networks of intersecting channels for performance of multiple successive or parallel integrated operations or reactions typically comprise planar structures to permit the incorporation of the more complex channel networks that are required. Simpler reactions, on the other hand, may be carried out in less complex systems, e.g., a single channel capillary.

In particularly preferred aspects, the substrates, and thus the overall structure of the microfluidic devices used in accordance with the present invention, are planar. Typically, such devices are fabricated from at least two different planar substrate layers. The channel or channels of the device are typically fabricated as grooves into one surface of one of the substrate layers. A second substrate layer is then overlaid and bonded onto the surface of the first, thereby sealing and defining the microscale channels of the device between the two layers. Generally, at least one of the substrate layers has one or more holes or ports disposed through the planar substrate, such that the hole or port is in fluid communication with one or more of the microscale channels when the substrate layers are mated. These holes or ports are typically used both as fluid reservoirs for introducing fluids into the channels of the device, as well as providing electrical access, e.g., contact points for electrodes that are placed in electrical contact with the fluids contained in the device.

Examples of microfluidic devices employing these planar structures are described in copending U.S. patent application Ser. Nos. 08/977,528, filed Nov. 25, 1997, Ser. No. 08/845,754, filed Apr. 25,1997 and Ser. No. 60/060,902, filed Oct. 3, 1997, each of which is incorporated herein by reference in its entirety for all purposes. Three layer substrate structures may also be employed having an optional third interior layer placed between the first and second planar layers, where the interior layer defines the side walls of the channels of the device while the first and second layers make up the top and bottom walls of the channels, respectively.

The electrical access ports are useful in heating applications, as is discussed in greater detail below, as well as in the transport and direction of materials through the channels that are contained in the device. In particular, in preferred aspects, the microfluidic devices and systems that are used in practicing the present invention employ electrokinetic material transport systems. These electrokinetic transport systems utilize controlled electrokinetic forces, e.g. electrophoretic and/or electroosmotic, to controllably move materials and fluids through the channels and their respective intersections. Examples of controlled electrokinetic transport in microfluidic systems are described in e.g., published PCT Application No. 96/04547, to Ramsey, which is incorporated herein by reference.

Once the liquid reactants are placed into the microscale channels, superheating is initiated by applying an effective level of an appropriate energy source for heating the contents of the channel or channels. A variety of energy sources may optionally be used to heat the fluid within the channels of the microfluidic device. For example, the contents of the microscale channels may be heated using conductive methods, e.g., by applying thermal energy to the external surfaces of the body structure of the microfluidic element, e.g., substrate or capillary. A variety of thermal energy sources may be readily utilized in this capacity. For example, in a simple aspect, the body of the device may be placed into an oven or adjacent to or in contact with a heating element, such that the body structure and thus the contents of the channels disposed within the body structure are heated to superheated levels. Examples of suitable heating elements are well known to those of skill in the art, and range from simple laboratory hot plates, heating blocks or ovens, to resistive thin film heating elements that may be integrated into an internal or external surface of a microfluidic device or within an appliance adapted for use with the device, e.g., into which the device is inserted.

Alternative energy sources can also be readily utilized in heating the contents of microscale channels, including, e.g., light sources such as lasers, lamps and the like, which can be directed at the channels of the device, and preferably, precisely directed at the channels within a microfluidic device where superheating is desired.

As noted above, however, in preferred aspects, the microfluidic devices described herein have electrodes associated with the channels of the device. As such, it is generally preferred to utilize electrical energy in superheating the contents of the channels of the device by resistive methods. Not only does this provide advantages of efficiency, e.g., in using a preexisting energy interface in the electrodes, but it also provides a more precise method of controlling and monitoring the temperature within the system. Specifically, applying a current through the liquid content of a reaction channel results in a resistive heating of that liquid.

Electrical resistive heating of fluids in microscale channels is described in substantial detail in U.S. patent application Ser. No. 08/977,528, filed Nov. 25, 1997 (Attorney Docket No. 100/01310), which is incorporated herein by reference. By applying enough current, e.g., a sufficient current density, through a given channel, the contents of that channel are superheated. Briefly, electric current passing through the fluid in a channel produces heat by dissipating energy through the electrical resistance of the fluid. Power dissipates as the current passes through the fluid, going into the fluid as energy over time to heat the fluid. The following mathematical expression generally describes a relationship between power, electrical current, and fluid resistance:

$$POWER = I^2 R$$

where POWER=power dissipated in fluid; I=electric current passing through fluid; and R=electric resistance of fluid. The above equation provides a relationship between power dissipated ("POWER"), current ("I") and resistance ("R").

Thus, temperature within a given channel can be increased by either increasing the resistance of the channel or increasing the amount of current passing through the channel, or a combination of the two. Increasing resistance of a channel can be readily accomplished by narrowing the cross-sectional area of the channel through which the current is applied. Further, by increasing the resistance and/or current within a channel to sufficiently high levels, one can achieve superheated temperatures within the channels of the device.

In preferred aspects, sufficient current densities are achieved by using one or both of (1) narrowed channel cross-sectional areas, and (2) increased applied current through the fluid. A simplified example of a microfluidic device having a channel with a region of narrowed cross-sectional area is shown in FIG. 1. In particular, as shown in FIG. 1, a microfluidic device 100 comprises a body structure 102, typically fabricated from two overlaid and bonded planar substrates (not separately shown) where one substrate has a series of channels 104, 106, 108 and 110, etched into one planar surface. Overlaying the second substrate provides the cover and sealing wall for the etched channels, forming conduits between the substrate layers. Each of the channels shown, e.g., channel 106, include a region of narrowed cross-sectional area (112) relative to the remaining regions of the channel 114. Reservoirs, e.g., reservoirs 116 and 118, are disposed at the termini of the channels, typically as apertures disposed through the overlaying planar substrate, for fluid introduction and to provide electrical access to the channel.

As noted above, one or both of the channel cross-sectional area or the applied current can be varied to elevate the temperature of fluid within the channel. As such, microscale channels for use in carrying out superheated reactions according to the present invention may fall within a wide range of suitable cross-sectional areas. Similarly, the currents applied to such channels are similarly widely variable. However, in preferred microfluidic systems, e.g., those having typical non-heating channel dimensions in the microscale range, as set forth above, where it is desired to heat fluids to superheated temperatures, the cross-sectional area of the channels or channel regions in which heating is desired will typically range from 10 $\mu m^2$ to about 500 $\mu m^2$. This corresponds to channels having dimensions of, e.g., from about 10 $\mu$m wide by 1 $\mu$m deep, to about 50 $\mu$m wide by 10 $\mu$m deep. However, wider and deeper channels my also be used.

Similarly, currents applied to the fluids within such narrowed channels typically range from about 5 $\mu$A to about 500 $\mu$A, and preferably from about 10 $\mu$A to about 100 $\mu$A.

The systems of the invention typically include a controller operably coupled to the energy source, for monitoring and controlling the temperature within the reaction channels of the device. This is particularly useful in those instances where reaction temperatures are desired that far exceed the expected boiling point of the fluid reactants. Specifically, careful monitoring and control of applied energy better allows maintenance of superheated temperatures without overshooting the desired temperature and/or inadvertently boiling the fluid reactants, and thereby fouling the channels of the device.

The controller aspect of the system typically includes a processor, e.g., a computer, that is appropriately programmed to receive temperature data from a sensor placed in thermal communication with the device or its fluid contents. The processor is also typically coupled to the energy source that delivers the heating energy to the device, e.g., the oven, hot plate, resistive heater, or electrical power supply. The processor is also appropriately programmed to instruct the energy source to increase or decrease the amount of applied energy depending upon whether the sensed temperature of the fluid within the device is above or below a set point temperature, e.g., chosen by the user. The processor may further include appropriate programming that indicates whether the fluid within the device is beginning to boil, e.g., as indicated by a significant, sudden increase in the resistance of the channel.

The sensor aspect of the controller is typically coupled to the processor, and is in contact with the channels of the device, and preferably, with the fluid content of those channels. Such sensors may include traditional thermal sensors, such as thermocouples, thermistors, IC. temperature sensors. In preferred aspects, however, the temperature within the channels is determined from the conductivity of the fluid disposed therein, which is dependent in part upon the fluid temperature (See U.S. application Ser. No. 08/977, 528, filed Nov. 25, 1997 (Attorney Docket No. 100/01310) and previously incorporated herein). As such, the sensor aspect of the controller typically comprises electrodes placed into electrical contact with different points of the microscale channels of the device. Preferably, the same electrodes used for heating and/or for material transport/ direction are utilized to determine the conductivity of the fluid, and thus the temperature.

The methods and systems of the invention have broad applicability. For example, as noted above, many reactions that progress faster at higher temperatures can be carried out in accordance with the present invention at still faster rates. For example, performance of the polymerase chain reaction for amplification of nucleic acids generally utilizes temperatures approaching the boiling point of the aqueous reactants, e.g., in the range of 95 to 100° C., in order to expedite the process of denaturing hybridized strands of template nucleic acids. However, such reactions are generally further expedited at superheated temperatures, without adverse effects on the overall reaction.

Similarly, a number of reactions, e.g., enzyme assays, require the denaturation of certain enzyme components of the material to be tested, prior to performance of the overall reaction, so that those components do not interfere with the desired reaction. The ability to superheat the reaction components, in situ, permits the performance of such denaturation more quickly and efficiently. Similarly, such superheated temperatures are also useful in the destruction and/or lysis of cells for performance of cell-based operations, e.g., preparative or analytical.

The present invention is further illustrated with reference to the following nonlimiting examples.

EXAMPLES

A planar microfluidic device having the channel geometry illustrated in FIG. 1 was used in each of the following superheating examples. Reagents were introduced into the channels of the device by placing the reagents into the reservoirs and allowing capillary action to draw the reagents through the channels.

The present invention is further illustrated with reference to the following nonlimiting examples.

Example 1
Conductive Superheating in Microfluidic Systems

PCR buffer was placed into the channel of the device that included a narrowed region that was 20 $\mu$m wide ×5 $\mu$m deep, by 2 mm long (channel 106 in FIG. 1), and mineral oil was placed over the buffer in the reservoirs (reservoirs 116 and 118) to reduce evaporative losses within the reservoirs.

Temperature changes within the fluid filled channel were monitored by measuring the conductivity of the fluid. At room temperature, the conductivity measured at 41.8 nA when a 1V potential was applied.

Figure 2:
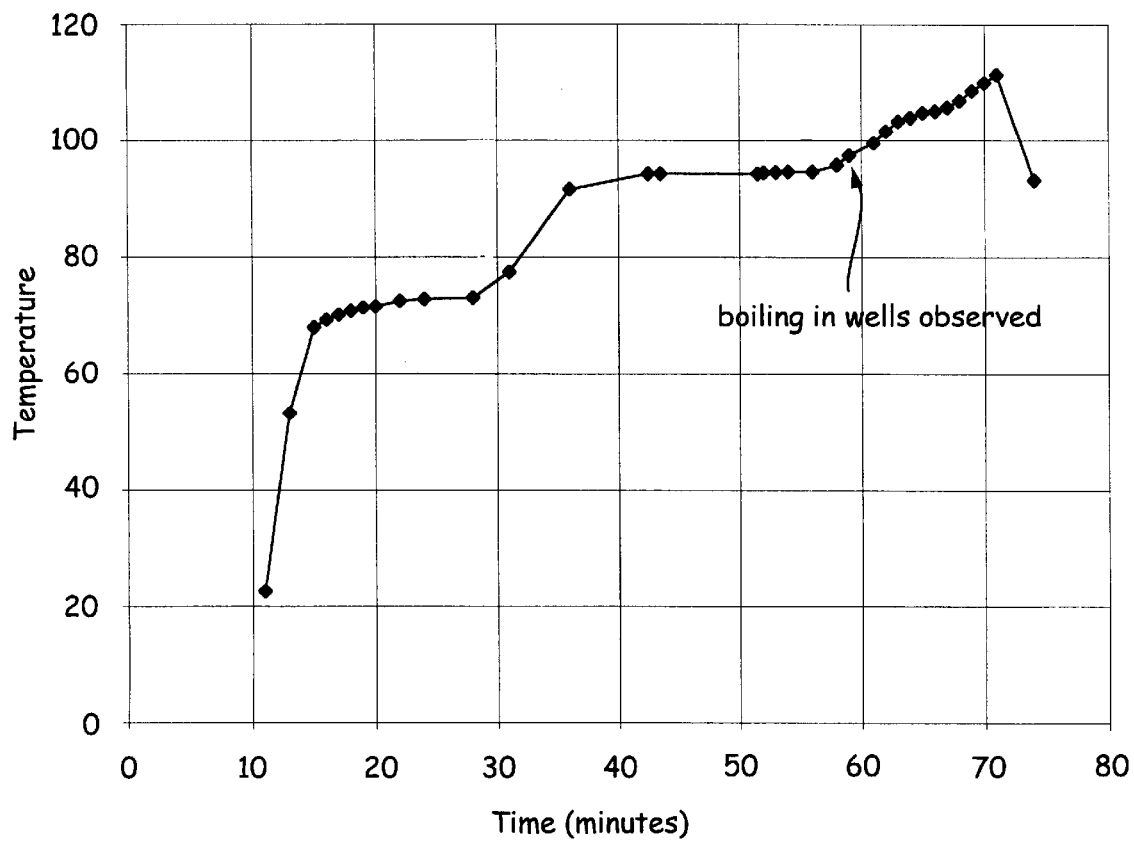
FIG. 2 is a temperature profile for fluids disposed within microscale channels of a microfluidic device while the device was globally heated in an oven.

The substrate was placed in an oven at 100° C. for approximately one hour, at which point the temperature of the oven was increased above 100° C. FIG. 2 shows a plot of the temperature of the fluid within the channels over the duration of the experiment. The arrows above the plot indicate the point at which the oven temperature was raised to the next incremental setting. Boiling of the fluid within the reservoirs was visually observed at just above 100° C., however, no boiling was observed within the channel, as shown by the labeled arrow below the plot. This was confirmed by measuring the conductivity of the fluid within the channels after removal from the oven. Specifically, production of bubbles within the channel would have resulted in a substantial decrease in the conductivity of that channel, as even small bubbles will significantly constrict the channels used, e.g., having narrow dimensions of 20 $\mu$m ×5 $\mu$m. However, conductivity through the channels did not decrease.

Example 2
Resistive Superheating in Microfluidic Systems

PCR buffer was again placed into a channel (channel 106) of a microfluidic device having the channel geometry shown in FIG. 1 as described above, and the conductivity of the buffer at room temperature was determined. Electrodes were placed into the reservoirs at the termini of the channel network. The electrodes were coupled to an electrical power supply having a 100 $\mu$A, 1000V capability, for passing current through the channel network and for concomitantly determining the conductivity of the fluid through the channels. The temperature of the fluid within the channels was estimated from the conductivity of the solution using a calibration table.

Figure 3:
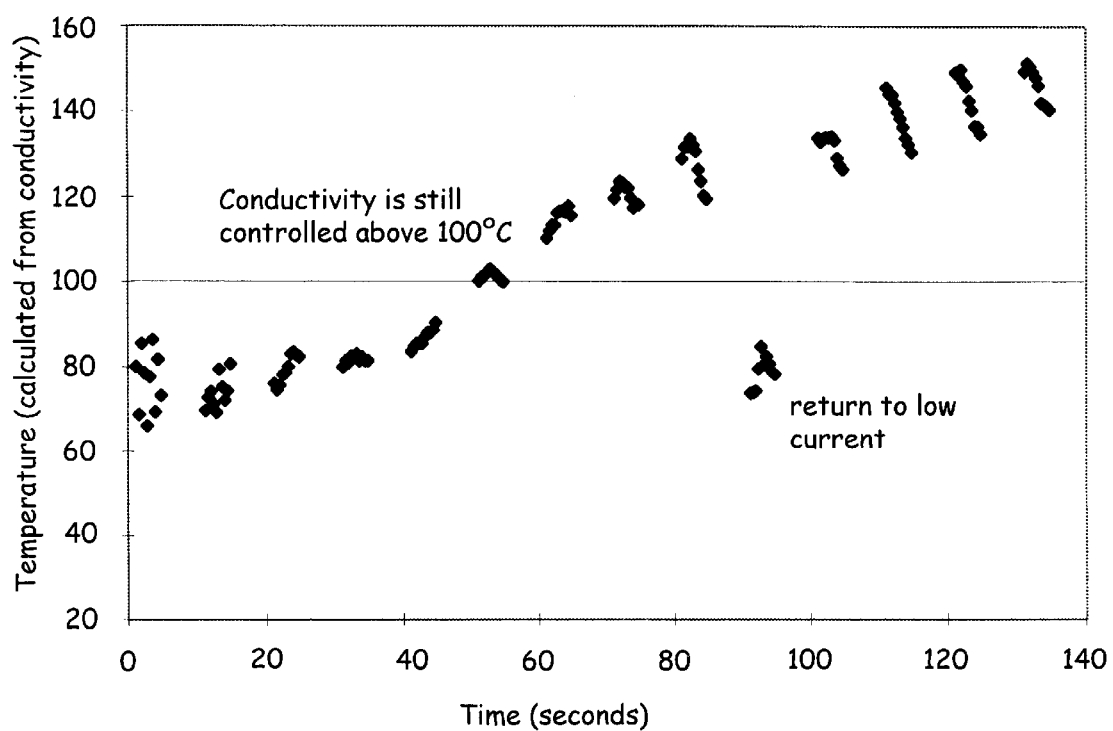
FIG. 3 is a profile of the temperature of fluid, as calculated from the fluid conductivity, in a microscale channel versus time while increasing current was incrementally applied through the channel.

The device was placed upon a hot plate at between 65 and 70° C. to elevate the ambient temperature of the device and minimize the amount of current required to superheat the fluid in the channels. The current applied through the channel was stepped up over time from a minimum of 2 μA to a maximum of 80 μA. During the experiment, the applied current was stepped up over time to: 2, 5, 10, 20, 30, 40, 50, 55, 60, 65, 70, 75 and 80 μA. A plot of fluid temperature (from calibrated conductivity) versus the time period of the experiment is shown in FIG. 3. The temperature of the fluid within the channel of the device increased over time from a measured temperature of 70° C., which was substantially equal to the temperature of the hot plate as measured by conventional means, to a temperature of approximately 140 to 150° C. For an aqueous buffer at or near sea level, this represents superheating of the fluid by 40 to 50° C. The ability to monitor temperature within the channel by the conductivity through that channel indicates a lack of bubble formation within the channel, as noted above.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method for performing at least one reaction at superheated temperature, comprising:
    placing at least a first reactant contained in a fluid in a microscale fluidic channel; and
    applying an energy to the fluid in the microscale channel, whereby the fluid is heated to a superheated temperature without boiling the fluid and further whereby a reaction occurs within said channel.

2. The method of claim 1, further comprising the step of removing the energy applied to the fluid in the microscale channel to permit cooling of the fluid in the channel.

3. The method of claim 2, comprising repeating the applying and removing steps, to thermally cycle the fluid in the microscale channel.

4. A method for performing at least one reaction at superheated temperature, comprising:
    placing at least a first reactant contained in a fluid in a microscale fluidic channel; and
    applying an energy to the fluid in the microscale channel, whereby the fluid is heated to a superheated temperature without boiling the fluid whereby a reaction occurs-within the channel, and further wherein the applying step comprises delivering an electrical current through the microscale channel sufficient to superheat the fluid in the microscale channel.

5. The method of claim 1, wherein the applying step comprises applying heat energy to the microscale channel to superheat the fluid in the channel.

6. The method of claim 1, wherein the first reactant comprises a nucleic acid, and the reaction to be performed is a melting reaction.

7. The method of claim 1, wherein the first reactant is a nucleic acid, and the reaction to be performed is an amplification reaction.

8. The method of claim 7, wherein the amplification reaction is selected from PCR (polymerase chain reaction) and LCR (ligase chain reaction).

9. A method of performing a reaction at a superheated temperature, the method comprising;
    providing a substrate having at least a first microscale channel disposed therein, said substrate being in communication with an energy source for delivering a sufficient level of energy to contents of the microscale channel to heat said contents to superheated temperatures;
    placing at least a first reactant into said microscale channel;
    applying a sufficient level of energy from said energy source to said microscale channel to heat said contents to superheated temperatures without boiling the contents, thereby causing a reaction to occur within said channel.

10. The method of claim 9, wherein in said providing step, said energy source is a thermal energy source disposed in thermal communication with said substrate.

11. The method of claim 9, further comprising the step of monitoring a temperature of the contents of the microscale channel during the reaction.

12. The method of claim 9, wherein in the providing step, the substrate comprises a silica substrate.

13. The method of claim 12, wherein the silica substrate comprises a silica capillary.

14. A method of performing a reaction at a superheated temperature, the method comprising:
    providing a substrate having at least a first microscale channel disposed therein, wherein the substrate comprises:
    a planar substrate having at least a first planar surface, the first microscale channel fabricated into the first planar surface; and
    a second planar substrate having at least a first planar surface, the first planar surface of the second planar substrate overlaying and bonded to the first planar surface of first planar substrate, defining the first microscale channel therebetween, said substrate being in communication with an energy source for delivering a sufficient level of energy to contents of the microscale channel to heat said contents to superheated temperatures;
    placing at least a first reactant into said microscale channel; and
    applying a sufficient level of energy from said energy source to said microscale channel to heat said contents to superheated temperatures without boiling the contents thereby causing a reaction to occur within the channel.

15. The method of claim 14, wherein at least one of the first and second planar substrates comprises a silica substrate, and the microscale channel is etched into the first planar surface of the first planar substrate.

16. The method of claim 14, wherein at least one of the first and second planar substrates comprise polymeric substrates.

17. The method of claim 9, wherein in the providing step, the energy source comprises a heating element disposed in thermal contact with the microscale channel for delivering thermal energy to the microscale channel, the thermal energy heating a fluid in the channel to a superheated temperature.

18. A system for performing at least one reaction at superheated temperature, comprising:
    a microfluidic device comprising:
    at least a first substrate;
    a microscale channel disposed in the substrate, the microscale channel having at least first and second unintersected termini;
    a heating system for applying energy to the microscale channel to heat a fluid in the channel to superheated temperatures, without boiling the fluid in the channel; and a controller for maintaining energy applied from the heating system to the microscale channel.

19. The system of claim 18, wherein the first substrate comprises a silica substrate.

20. The system of claim 18, wherein the silica substrate is a silica capillary.

21. A system for performing at least one reaction at superheated temperature, comprising:
a microfluidic device comprising:
at least a first substrate comprising:
a planar substrate having at least a first planar surface, a first microscale channel fabricated into the first planar surface; and
a second planar substrate having at least a first planar surface, the first planar surface of the second planar substrate overlaying and bonded to the first planar surface of first planar substrate, defining the first microscale channel therebetween, the first microscale channel having at least first and second unintersected termini;
a heating system for applying energy to the microscale channel to heat a fluid in the channel to superheated temperatures, without boiling the fluid in the channel; and
a controller for maintaining energy applied from the heating system to the microscale channel.

22. The system of claim 21, wherein at least one of the first and second planar substrates comprises a silica substrate, and the microscale channel is etched into the first planar surface of the first planar substrate.

23. The system of claim 21, wherein at least one of the first and second planar substrates comprises a polymeric substrate.

24. A system for performing at least one reaction at superheated temperatures, comprising:
a microfluidic device comprising at least a first substrate, a microscale channel disposed in the substrate, the microscale channel having at least first and second unintersected termini;
a heating system for applying energy to the microscale channel to heat a fluid in the channel to superheated temperatures, without boiling the fluid in the channel, which, heating system comprises:
first and second electrodes disposed in electrical contact with the first and second unintersected termini of the microchannel; and
a controller for maintaining energy applied from the heating system to the microscale channel, wherein the controller comprises an electrical controller separately electrically coupled to each of the first and second electrodes, the electrical controller delivering an electrical current between the first and second electrodes, the electrical current elevating a temperature of a fluid in the microscale channel without boiling the fluid in the channel.

25. The system of claim 24, further comprising a sensor for determining a temperature of a fluid in the microscale channel.

26. The system of claim 25, wherein the sensor comprises a conductivity sensor integrated into the electrical controller.

27. The system of claim 18, wherein the heating system comprises a heating element disposed in thermal contact with the microscale channel for delivering thermal energy to the microscale channel, the thermal energy heating a fluid in the channel to a superheated temperature.

28. The system of claim 18, further comprising a sensor for determining a temperature of a fluid in the microscale channel.

29. A system for performing at least one reaction at superheated temperature, comprising:
a microfluidic device comprising:
at least a first substrate;
a microscale channel disposed in the substrate, the microscale channel having at least first and second unintersected termini;
a heating system for applying energy to the microscale channel to heat a fluid in the channel to superheated temperatures, without boiling the fluid in the channel;
the heating system comprises first and second electrodes disposed at the first and second unintersected termini of the first channel, and a conductivity sensor operably coupled to the first and second electrodes for measuring a conductivity between the first and second electrodes; and
a controller for maintaining energy applied from the heating system to the microscale channel.

30. The method of claim 4, wherein the first reactant comprises a nucleic acid, and the reaction to be performed is a melting reaction.

31. The method of claim 4, wherein the first reactant is a nucleic acid, and the reaction to be performed is an amplification reaction.

32. The method of claim 31, wherein the amplification reaction is selected from PCR (polymerase chain reaction) and LCR (ligase chain reaction).

33. The method of claim 4, further comprising the step of monitoring a temperature of the contents of the microscale channel during the reaction.

34. The method of claim 14, wherein the first reactant comprises a nucleic acid, and the reaction to be performed is a melting reaction.

35. The method of claim 14, wherein the first reactant is a nucleic acid, and the reaction to be performed is an amplification reaction.

36. The method of claim 35, wherein the amplification reaction is selected from PCR (polymerase chain reaction) and LCR (ligase chain reaction).

37. The method of claim 14, further comprising the step of monitoring a temperature of the contents of the microscale channel during the reaction.

38. The method of claim 14, wherein in the providing step, at least one of the first and second substrates comprise a silica substrate.

39. The system of claim 14, wherein the heating system comprises a heating element disposed in thermal contact with the microscale channel for delivering thermal energy to the microscale channel, the thermal energy heating a fluid in the channel to a superheated temperature.

40. The system of claim 21, further comprising a sensor for determining a temperature of a fluid in the microscale channel.

41. The system of claim 24, wherein the first substrate comprises a silica substrate.

42. The system of claim 24, wherein the silica substrate is a silica capillary.

43. The system of claim 29, wherein the first substrate comprises a silica substrate.

44. The system of claim 29, wherein the silica substrate is a silica capillary.

45. The system of claim 29, wherein the heating system comprises a heating element disposed in thermal contact with the microscale channel for delivering thermal energy to the microscale channel, the thermal energy heating a fluid in the channel to a superheated temperature.

* * * * *

UNITED STATES PATENT AND TRADEMARK OFFICE
CERTIFICATE OF CORRECTION

PATENT NO. : 6,420,143 B1
DATED : July 16, 2002
INVENTOR(S) : Kopf-Sill

It is certified that error appears in the above-identified patent and that said Letters Patent is hereby corrected as shown below:

Column 12,
Line 46, please delete "14" and insert -- 21 --.

Signed and Sealed this

Twenty-fourth Day of December, 2002

JAMES E. ROGAN
*Director of the United States Patent and Trademark Office*